US00RE39155E

(19) United States
(12) Reissued Patent
Belleau et al.

(10) Patent Number: US RE39,155 E
(45) Date of Reissued Patent: Jul. 4, 2006

(54) USE OF 1,3-OXATHIOLANE NUCLEOSIDE ANALOGUES IN THE TREATMENT OF HEPATITIS B

(75) Inventors: Bernard Belleau, deceased, late of Westmont (CA); by Pierrette Belleau, legal representative, Montreal (CA); Nghe Nguyen-Ba, La Praire (CA)

(73) Assignee: Shire BioChem Inc., Quebec (CA)

(21) Appl. No.: 09/585,431

(22) PCT Filed: Jan. 3, 1992

(86) PCT No.: PCT/CA92/00001

§ 371 (c)(1),
(2), (4) Date: Aug. 9, 1993

(87) PCT Pub. No.: WO92/11852

PCT Pub. Date: Jul. 23, 1992

Related U.S. Patent Documents

Reissue of:
(64) Patent No.: 5,532,246
Issued: Jul. 2, 1996
Appl. No.: 08/084,222
Filed: Aug. 9, 1993

(30) Foreign Application Priority Data

Jan. 3, 1991 (GB) ..... 9100039
May 7, 1991 (GB) ..... 9109913

(51) Int. Cl.
*A61K 31/505* (2006.01)

(52) U.S. Cl. ..... 514/274
(58) Field of Classification Search ..... 514/274
See application file for complete search history.

(56) References Cited

U.S. PATENT DOCUMENTS 5,039,667 A * 8/1991 Tyrrell et al. ..... 514/45
5,047,407 A * 9/1991 Belleau et al. ..... 514/274

FOREIGN PATENT DOCUMENTS

| | | | | |
|---|---|---|---|---|
| EP | 0206497 | A2 * | 12/1986 | |
| EP | 0302760 | B * | 6/1988 | |
| EP | 0349242 | A2 * | 1/1990 | |
| EP | 0382526 | A2 * | 8/1990 | |
| EP | 0421739 | A1 * | 4/1991 | |
| EP | 0421777 | A1 * | 4/1991 | |
| EP | 0421819 | A1 * | 4/1991 | |
| EP | 0505181 | A1 * | 9/1992 | |
| EP | 0515144 | A1 * | 11/1992 | |
| GB | 2230266 | * | 10/1990 | |
| WO | WO89/04662 | * | 6/1989 | ..... 31/66 |
| WO | 2230266 | A * | 10/1990 | |
| WO | WO90/12023 | * | 10/1990 | |
| WO | WO92/16215 | * | 10/1990 | |
| WO | WO90/14079 | * | 11/1990 | |
| WO | WO90/14091 | * | 11/1990 | |
| WO | WO91/00282 | * | 2/1991 | |
| WO | WO91/01137 | * | 2/1991 | |
| WO | WO91/01326 | * | 2/1991 | |
| WO | WO91/11186 | * | 8/1991 | |
| WO | WO91/17159 | * | 11/1991 | |
| WO | WO92/08717 | * | 5/1992 | |
| WO | WO92/14743 | * | 9/1992 | |
| WO | WO92/15308 | * | 9/1992 | |
| WO | WO92/18517 | * | 10/1992 | |
| WO | WO92/19246 | * | 11/1992 | |

OTHER PUBLICATIONS

Kassianides et al., Abstract: "Effects of 2',3'–dideoxycytidine on Duck Hepatitis B Virus," 94 Gastroenterology No. 5, A552 (1988).*

Beach et al., "Synthesis of Enantiomerically Pure (2'R, 5'S–(–)–1–[1–(Hydroxymethyl)–oxathiolan–5–yl]cytosine as a Potent Antiviral Agent Against Hepatitis B Virus (HBV) and Human Immunodeficiency Virus (HIV)", 57 J. Org. Chem., pp. 2217–2219 (1992).*

Belleau et al., "Design and Activity of a Novel Class of Nucleoside Analogs Effective Against HIV–1", Fifth International Conference on AIDS, Montreal, Canada, Abstract T.C.O.1 (1989).*

Carlisle et al., "Cellular Pharmacology of the Anti–HIV Agent BCH–189 (2'–Deoxy–3'–Thiacytidine) in Human Peripheral Blood Mononuclear Cells (PBMC)", American Association for Cancer Research Proceedings, 31 Abstract 2435 (1990).*

Chang et al., "Deoxycytidine Deaminase–resistant Stereoisomer is the Active Form of (+/–)–2',–3'–diedeoxy–3'–thiacytidine in the Inhibition of the Hepatitis B Virus Replication", 267 J. Biol. Chem., pp. 3938–3942 (1992).*

Coats et al., "The Separated Enantiomers of 2'–Deoxy–3'–Thiacytidine (BCH 189) both Inhibit Human Immunodeficiency Virus Replication in Vitro", 36 Antimicrobial Agents & Chemotherapy, No. 1, pp. 202–205 (1992).*

(Continued)

*Primary Examiner*—Raymond J. Henley, III
(74) *Attorney, Agent, or Firm*—millen, White, Zelano, Branigan, P.C.

(57) ABSTRACT

Use of a compound of formula (I) or a pharmaceutically acceptable derivative thereof in the manufacture of a medicament for the treatment of hepatitis B is disclosed.

(I)

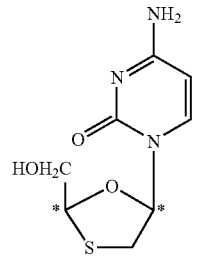

18 Claims, No Drawings

OTHER PUBLICATIONS

Doong et al., "Inhibition of the Replication of Hepatitis B Virus In–Vitro by 2'3' Dideoxy–3'–thiacytidine and Related Analogues", Thirty–first Annual Interscience Conference of Antimicrobial Agents and Chemotherapy, Chicago, IL, USA, Sep. 29–Oct. 2, 1991.*

Doong et al., "Inhibition of the Replication of Hepatitis B Virus in vitro by 2'3–dideoxy–3'–thiacytidine and related analogues", 88 Proc. Natl. Acad. Sci., USA, pp. 8495–8499; 88 Physiology/Pharmacology 8495–8499 (1991).*

Greenberg et al., "Metabolism, Toxicity, and Anti–HIV and B Cell Lines", 616 Annals of the New York Academy of Sciences, 517–518 (1990).*

Kassianides et al., "Inhibition of Duck Hepatitis B Virus Replication by 2'3'–dideoxycytidine", 97 Gastroenterology, No. 5, 1275–1280 (1989).*

Lee et al., "In Vitro and In Vivo Comparisons of the Abilities of Purine and Pyrimidine 2',3'–Dideoxynucleosides To Inhibit Duck Hepadnavirus", 33 Antimicrobial Agents and Chemotherapy, No. 3, 336–39 (1989).*

Soudeyns et al., "Anti–Human Immunodeficiency Virus Type 1 Activity and In Vitro Toxicity of 2'–Deoxy–3'–Thiacytidine (BCH–189), a Novel Heterocyclic Nucleoside Analog", 35 Antimicrobial Agents and Chemotherapy, No. 7, pp 1386–1390 (1991).*

Suzuki et al., "Inhibition of Hepatitis B Virus Replication By Purine 2',3'–Dideoxynucleosides", 156 Biochemical and Biophysical Research Communications, 1144–1151 (1988).*

Wainberg et al., Abstract, "Anti–HIV–1 Activity, Toxicity and Pharmacokinetics of Totally Novel Nucleoside Analogs", M.C.P. 63, V International Conference on AIDS, Montreal, Quebec, Canada, Jun. 4–9, 1989.*

Wainberg et al., "Characterization of AZT–Resistant Isolates of HIV–1: Susceptibility to Deoxythiacytidine and other Nucleosides", VI International Conference on AIDS, San Francisco, CA, vol. 3, ABstract SB87, p. 117 (1990).*

Sandrstrom et al., "Antiviral Therapy in AIDS: Clinical Pharmacological Properties and Therapeutic Experience to Date", 34 Drugs, pp 372–390 (1987).*

Varmus, "A Growing Role for Reverse Transcription", 299 Nature, pp. 204–205 (1982).*

Higgins, PG, "Interferons", J. Clin. Pathol., 1984; 37:109–116.*

* cited by examiner

USE OF 1,3-OXATHIOLANE NUCLEOSIDE ANALOGUES IN THE TREATMENT OF HEPATITIS B

Matter enclosed in heavy brackets [ ] appears in the original patent but forms no part of this reissue specification; matter printed in italics indicates the additions made by reissue.

This application is a 371 of PCT/CA92/00001 filed Jan. 3, 1992.

The present invention relates to the use of nucleoside analogues in the treatment of viral infections. More specifically it is concerned with the use of 1,3-oxathiolane nucleoside analogues in the treatment of hepatitis, in particular hepatitis B.

Hepatitis B is a viral disease transmitted orally or parenterally by contaminated material such as blood and blood products, contaminated needles, sexually and vertically from infected or carrier mothers to their offspring. In those areas of the world where the disease is common vertical transmission at an early age results in a high proportion of infected individuals becoming chronic carriers of hepatitis B. There are an estimated 280,000,000 carriers of hepatitis B worldwide. At the present time there are no effective chemotherapeutic agents for the treatment of hepatitis B infections.

A number of nucleoside derivatives have been described as having activity against the hepatitis B virus.

EPA 0206497 describes a number of 2',3'-dideoxy purine and pyrimidine nucleosides with antiviral activity including activity against the hepatitis B virus.

EPA 0302760 describes the use of 2',3'-dideoxy purine nucleosides for the treatment of hepatitis B infections.

WO90/14079 describes the treatment of hepatitis B by administration of 2',3'-dideoxycytidine.

WO90/14091 describes the treatment of hepatitis B by administration of 2',3'-dideoxyguanosine, 2',3'-dideoxy adenosine or 2',3'-dideoxyinosine.

European patent application publication number 0 382 526 describes a series of 1,3-oxathiolane nucleoside analogues having antiviral activity, in particular activity against HIV, the causative agent of AIDS.

PCT patent application publication number WO91/17159 describes the compound (2R,cis)-4-amino-1-(2-hydroxymethyl-1,3-oxathiolan-5-yl)-(1H)-pyrimidin-2-one (also known as 3TC) and its use in the treatment of HIV infections. 3TC is the (−)-enantiomer of one of the compounds (BCH-189) described in EPA 0382526. We have now found that BCH-189 and its individual enantiomers, including 3TC, are active both in vitro and in vivo against the hepatitis B virus.

The invention accordingly provides, in a first aspect, a method for the treatment of an animal, including man, infected with or susceptible to infection with the hepatitis B virus comprising the administration of an effective amount of a compound of formula (I)

(I)

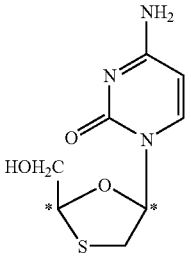

or a pharmaceutically acceptable derivative thereof.

In a further or alternative aspect there is provided a compound of formula (I) as defined hereinabove or a pharmaceutically acceptable derivative thereof for use in the manufacture of a medicament for the treatment of hepatitis B.

As will be appreciated by those skilled in the art references herein to treatment extend to prophylaxis as well as to the treatment of established infections or symptoms.

As will be appreciated by those skilled in the art the compound of formula (I) is a cis compound and contains two chiral centres (shown in formula (I) by *). Thus the compound exists as two enantiomers, compounds of formulae (Ia) an (Ib) respectively.

(Ia)

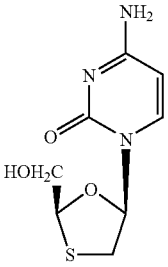

(Ib)

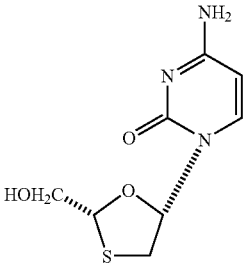

The compound of formula (I) is preferably in the form of a racemic mixture or its (−)-enantiomer but a mixture of compounds of formulae (Ia) and (Ib) in any ratio may be employed in the invention.

The compound of formula (I) has the chemical name cis-4-amino-1-(2-hydroxymethyl-1,3-oxathiolan-5-yl-(1H)-pyrimidin-2-one. It is also known as BCH-189. The (−)-enantiomer has the chemical name (−)-cis-4-amino-1-(2-hydroxymethyl-1,3-oxathiolan-5-yl)-(1H)-pyrimidin-2-one and has the absolute stereochemistry of the compound of formula (Ib) which has the name (2R,cis)-4-amino-1-(2-hydroxymethyl)-1,3-oxathiolan-5-yl)-(1H)-pyrimidin-2-one. It is also known as 3TC.

Preferably when the (−)-enantiomer is employed it will be substantially free of the corresponding (+)-enantiomer, that is to say no more than about 5% w/w of the (+)-enantiomer, preferably no more than about 2%, in particular less than about 1% w/w will be present.

By the term "pharmaceutically acceptable derivative" is meant any pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified, to provide pharmaceutically acceptable derivatives thereof, at functional groups in both the base moiety and at the hydroxymethyl group of the oxathiolane ring. Modification at all such functional groups are included within the scope of the invention. However, of particular interest are pharmaceutically acceptable derivatives (e.g. esters) obtained by modification of the 2-hydroxymethyl group of the oxathiolane ring.

Preferred esters of the compounds of formula (I) include the compounds in which OH is replaced by a carboxyl function

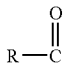

in which the non-carbonyl moiety R of the ester grouping is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); substituted dihydro pyridinyl (e.g. N-methyldihydro pyridinyl); sulphonate esters such as alkyl- or aralkylsulphonyl (e.g. methanesulphonyl); sulfate esters, amino acid esters (e.g. L-valyl or L-isoleucyl) and mono-, di- or tri-phosphate esters.

Also included within the scope of such esters are esters derived from polyfunctional acids such as carboxylic acids containing more than one carboxyl group, for example, dicarboxylic acids $HO_2C(CH_2)_nCO_2H$ where n is an integer of 1 to 10 (for example, succinic acid) or phosphoric acids. Methods for preparing such esters are well known. See, for example, Hahn et al., "Nucleotide Dimers as Anti Human Immunodeficiency Virus Agents", Nucleotide Analogues, pp. 156–159 (1989) and Busso et al., "Nucleotide Dimers Suppress HIV Expression In Vitro", AIDS Research and Human Retroviruses, 4(6), pp. 449–455 (1988).

With regard to the above described esters, unless otherwise specified, any alkyl moiety present advantageously contains 1 to 16 carbon atoms, particularly 1 to 4 carbon atoms and could contain one or more double bonds. Any aryl moiety present in such esters advantageously comprises a phenyl group.

In particular the esters may be a $C_{1-16}$alkyl ester, an unsubstituted benzoyl ester or a benzoyl ester substituted by at least one halogen (bromine, chlorine, fluorine or iodine), $C_{1-6}$alkyl, saturated or unsaturated $C_{1-6}$alkoxy, nitro or trifluoromethyl groups.

Pharmaceutically acceptable salts of the compounds of formula (I) include those derived from pharmaceutically acceptable inorganic and organic acids and bases. Examples of suitable acids include hydrochloric, hydrobromine, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

References hereinafter to a compound according to the invention include both the compound of formula (I) and its pharmaceutically acceptable derivatives.

The compound of formula (I) and its individual enantiomers may be prepared by any method known in the art for the preparation of compounds of analogous structure for example by the methods described in EPA 0 382 526 or WO91/17159 both of which are incorporated herein by reference.

The compound of formula (I) both as the racemic mixture and as the individual enantiomers has been found to inhibit the hepatitis B virus both in vitro and in vivo.

It will be appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 ng/kg of bodyweight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, preferably about 2 to 50 μM, most preferably about 3 to about 30 μM. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

A pharmaceutical formulation will comprise a compound of formula (I) or a pharmaceutically acceptable derivative thereof together with one or more pharmaceutical acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical formulations suitable for rectal administration wherein the carrier is a solid are most preferably presented as unit dose suppositories. Suitable carriers include cocoa butter and other material commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one or more dispersing agents, solubilising agents or suspending agents. Liquid sprays are conveniently delivered from pressurised packs.

For administration by inhalation the compounds according to the invention are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount.

Alteratively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions for use in the present invention may also contain other active ingredients such as antimicrobial agents, or preservatives.

Suitable formulations for use in the invention are described for example in EPA 0382526 and WO91/17159.

The compounds of the invention may also be used in combination with other therapeutic agents for example other antiinfective agents. In particular the compounds of the invention may be employed together with known antiviral agents.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The individual components of such combinations may be administered either sequentially or simultaneously in separate or combined pharmaceutical formulations.

When the compound of formula (I) or a pharmaceutically acceptable derivative thereof is used in combination with a second therapeutic agent active against the same virus the dose of each compound may be either the same as or differ from that when the compound is used alone. Appropriate doses will be readily appreciated by those skilled in the art.

The invention is illustrated by the following examples which should not be interpreted as a limitation of the invention.

EXAMPLE 1

Biological Activity (A) Newborn ducklings were infected with DHBV. After 5 to 7 days post-infection, samples of blood were taken from the ducklings and examined for DHBV DNA using dot hybridization with a specific DNA probe (Mason et al., Proc. Natl. Acad. Sci. USA 79, 3997–4001 (1982)). The livers were removed from dot-blot positive ducklings and used to produce primary hepatocye cultures infected with DHBV as previously described. (Tuttleman et al., J. of Virology, 58, 17–25). After 2 days in culture, antiviral agents were added to the culture media. The media were charged every 2 days and at selected times, the cells were removed and the total DNA extracted.

The DNA was spotted on nitrocellulose paper and probed with the $^{32}$P-labelled DHBV DNA probe in accordance with the following procedure. The DNA from DHBV-infected hepatocytes was extracted and spotted onto a nitrocellular filter. The above described $^{32}$P-nick translated-DHBV DNA (pDH-010=DHBV) probe was used. The DNA was extracted from 6-cm cell culture dishes at various times post-plating. In the VC group, cells were harvested at 2, 6, 8, 10, 14, 18 and 20 days. Duplicate samples were spotted for days 14, 18 and 20. In drug-treated groups, cells were harvested on days 8, 14 and 20. Drugs were added to the culture at 2 days post-plating and maintained throughout media changes every 2 days. The total intracellular DNA was extracted from cells using the standard phenol extraction method. The cells in a 6-cm diameter Petri dish (approximately $5\times10^6$ cells) were lysed in a lysis buffer containing 0.2% SDS, 150 mM Tris-HCl pH 8.0, 10 mM EDTA, 5 mM EGTA, and 150 mM NaCl. The cell lysate was digested with 0.5 mg/ml of pronase E (available from Sigma) at 37° C. for 2 hours and proteinized by extraction with an equal volume of phenol saturated with 20 mM Tris HCl, pH 7.5, 0.5 mM EDTA and 0.1% 8-hydroxyquinoline. Concentrated ammonium acetate (pH for 7.0 (2.5 M)) was added to the aqueous phase to yield a 0.25M ammonium acetate solution and the nucleic acids were precipitated with 2 volumes of 100% ethanol. The pellet of nucleic acid was washed with ethanol and dried. The DNA was dissolved in a solution containing 12.5 mM Tris HCl, pH 7.5, 10 mM EDTA, 30% glycerol and 0.01% bromophenol blue. One twelfth of the DNA sample was spotted onto the nitrocellulose for dot-blot analysis.

The drugs tested were scored on a scale of 0 (no activity) to ++++ (high activity).

The compounds tested were cis-2-amino-1-(-2-hydroxymethyl-1,3-oxathiolan-5-yl)-(1H)-pyrimidin-2-one (Compound of formula (I) both as the racemate and the (−)-enantiomer) and two known inhibitors of hepatitis B, 2',3'-dideoxy-guanosine (ddG) and 2,6-diaminopurine-9-β-D-2',3'-dideoxyribofuranoside (ddDAPR) European Patent Application Publication No. 0 302 760).

The results are shown in Table 1.

(B) Human Hepatitis B Results (i) Monolayers of Hep G2 cells transfected with human hepatitis B virus in 6-well plates in MEM supplemented with 380 μg/ml Geneticin (GIBCO no. 860-18111J, G418 Sulfate) and 10% fetal calf serum were prepared and the monolayers used when the cells were 75% confluent or greater.

Stock solutions of drugs were prepared in PBS at 1 mg/ml. For drugs not soluble to this extract, either the suspension was warmed to 42° C. and ethanol added or the drug dissolved at a lower final concentration.

Stock solutions of drugs were diluted to final concentrations of 10 μ/ml in MEM (supplemented as above).

Medium was removed from cell monolayers and replaced with freshly prepared medium containing the drugs. 2 ml/well and triplicate wells were used for each assay.

The medium was removed and replaced with fresh medium containing drugs every second day for 14 days (i.e., 7 changes of drugs solutions).

Medium was removed from each well and cells washed with 1 ml PBS. 2 ml/well RIPA buffer* was added, and cells removed from the wells by scraping with a rubber policeman. The cells were then transferred to test tubes.

*RIPA buffer 0.15M NaCl, 1% sodium deoxycholate, 1% Triton×100, 0.1% SDS, 0.01M Tris HCl, pH 7.4.

1 ml chloroform was added to each tube and mixed with a vortex mixer. Then 1 ml phenol (saturated with 20 mM Tris, 1 mM EDTA, and 0.1% hydroxyquinoline) was added to each tube, the tube centrifuged and 1 ml of aqueous layer removed.

Ammonium acetate to 0.2M was added and mixed followed by 2.5 volumes of ice cold ethanol. The mixture was left at −20° C. overnight to precipitate the DNA. DNA was pelleted by centrifugation and washed once in cold ethanol and dried.

The pellet was dissolved in 200 μl of Tris (10 mM) EDTA (1 mM) buffer by leaving overnight at 4° C. and sonicating briefly (20 seconds). 20 μl of each sample was dotted onto a nylon membrane and dot hybridized with an HBV DNA probe.

The results are shown in Table 2a.

(ii) The method used for this test is described in detail in Korba et al. Antiviral Research 15, 217–228, 1992, and summarised below.

Hep G2 cells transfected with human hepatitis B virus genomic DNA (2.2.15 cells) were grown and maintained in RPMI-1640 culture medium containing 5% foetal bovine serum, 2 mM glutamine and 50 μg/ml gentamicin sulphate, and checked routinely for G418 resistance. Cultures of 2.2.15 cells were grown to confluence in 24 well tissue culture plates and maintained for 2 to 3 days in that condition prior to drug treatment.

Drugs were dissolved in sterile water or sterile 50% DMSO in water at concentrations 100-fold higher than the highest test concentration. These solutions were diluted as needed in culture medium.

The culture medium on the confluent cells was changed 24 hours prior to exposure to test compounds. During the 10 day treatment the culture medium was changed daily. After 10 days of treatment the culture medium was collected and frozen at −70° C. for HBV DNA analysis.

To analyse extracellular HBV DNA, 0.2 ml samples of culture medium were incubated for 20 minutes at 25° C. in 1M NaOH/10X SSC (1X SSC is 0.15M NaCl/0.015 M Sodium Citrate, pH 7.2) and then applied to nitrocellulose membranes presoaked in 20X SSC using a blotting apparatus. Samples were neutralised by washing twice with 0.5 ml of 1M Tris, pH 7.2/2M NaCl and once with 5 ml of 20X SSC. Filters were then rinsed in 2X SSC and baked at 80° C. for 1 hour under vacuum.

A purified 3.2 kb EcoRl HBV DNA fragment was labelled with [$^{32}$P]dCTP by nick translation and used as a probe to detect HBV DNA on the dot-blot by DNA hybridisation. After washing, the hybridised blot was dried and $^{32}$P was quantified using an Ambis beta scanner.

The results are shown in Table 2b.

TABLE 1

Activity of compounds against Duck hepatitis B virus in vitro

| Compound | IC50 μg/ml Activity |
|---|---|
| Compound of formula (I) | |
| Racemate | ++++ at 10 μg/ml |
| (*)-enantiomer | <1 μg/ml |
| ddG | 0.07 μg/ml |
| ddDAPR | 0.07 μg/ml |

TABLE 2A

Activity of compounds against human hepatitis B virus in vitro

| | HBV Activity at 10 μg/ml |
|---|---|
| Compound of formula (I) | |
| Racemate | +++ |
| ddG | +++ |
| ddDAPR | + |

TABLE 2B

| | IC50 μM |
|---|---|
| 3TC | 5.6 |
| ddC | 2.2 |
| araAMP | 2.9 |
| cdG | 0.034 |

ddC = 2',3'-dideoxycytidine
cdG = carbocyclic deoxyguanosine
araAMP = adenosylarabinoside-5'-monophosphate

We claim:

1. A method for the treatment of *hepatitis B infection, in* a mammal, including a human, suffering from hepatitis B infection, comprising administration of an effective amount of a compound of formula (I)

(I)

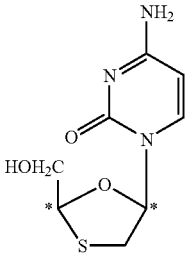

or a pharmaceutically acceptable salt, ester, or salt of an ester thereof to said mammal.

2. The method according to claim 1 wherein the hepatitis B infection is human hepatitis B.

3. The method according to claim 1 wherein the compound of formula (I) comprises (±)-cis-4-amino-1-(2-hydroxymethyl-1,3-oxathiolan-5-yl)-(1H)-pyrimidin-2-one or a pharmaceutically acceptable salt, ester, or salt of an ester thereof.

4. The method according to claim 1 wherein the compound of formula (I) comprises (−)-cis-4-amino-1-(2-hydroxymethyl-1,3-oxathiolan-5-yl)-(1H)-pyrimidin-2-one or a pharmaceutically acceptable salt, ester, or salt of an ester thereof.

5. The method according to claim 4 wherein the compound of formula (I) is substantially free of the corresponding (+)-enantiomer.

6. The method according to any one of claims 1 to 5 wherein the compound of formula (I) is adapted for oral administration.

7. The method according to any one of claims 1 to 5 wherein the compound of formula (I) is adapted for parenteral administration.

8. The method according to any one of claims 1 to 5 wherein the compound of formula (I) is in unit dosage form.

9. The method according to claim 8 wherein the compound is present in an amount of from 10 to 1500 mg.

*10. A method for the treatment of hepatitis B infection, in a human, suffering from hepatitis B infection, comprising administering to said human an effective amount of a compound of formula (I)*

*(I)*

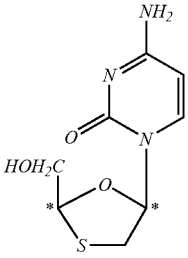

*or a pharmaceutically acceptable salt, ester, or salt of an ester thereof.*

*11. The method according to claim 10, wherein the compound of formula (I) is (−)-cis-4-amino-1-(2-hydroxymethyl-1,3-oxathiolan-5-yl)-(1H)-pyrimidin-2-one or a pharmaceutically acceptable salt, ester or salt of an ester thereof.*

*12. A method for the treatment of hepatitis B infection, in a human, suffering from hepatitis B infection, comprising administering to said human an effective amount of a compound of formula (I)*

*(I)*

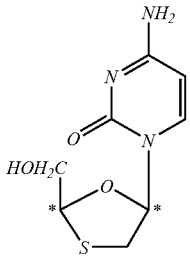

*or a pharmaceutically acceptable salt thereof.*

*13. The method according to claim 12, wherein the compound of formula (I) is (−)-cis-4-amino-1-(2-hydroxymethyl-1,3-oxathiolan-5-yl)-(1H)-pyrimidin-2-one or a pharmaceutically acceptable salt thereof.*

*14. The method according to claim 10, comprising administering a compound of formula (I).*

*15. The method according to claim 13, comprising administering (−)-cis-4-amino-1-(2-hydroxymethyl-1,3-oxathiolan-5-yl)-(1H)-pyrimidin-2-one.*

*16. The method according to claim 11, wherein the (−)-cis-4-amino-1-(2-hydroxymethyl-1,3-oxathiolan-5-yl)-(1H)-pyrimidin-2-one or pharmaceutically acceptable salt thereof is substantially free of the corresponding (+)-enantiomer.*

*17. The method according to claim 13, wherein the (−)-cis-4-amino-1-(2-hydroxymethyl-1,3-oxathiolan-5-yl)-(1H)-pyrimidin-2-one or pharmaceutically acceptable salt thereof is substantially free of the corresponding (+)-enantiomer.*

*18. The method according to claim 15, wherein the (−)-cis-4-amino-1-(2-hydroxymethyl-1,3-oxathiolan-5-yl)-(1H)-pyrimidin-2-one is substantially free of the corresponding (+)-enantiomer.*

* * * * *